United States Patent [19]

Rivier et al.

[11] 4,428,942

[45] Jan. 31, 1984

[54] ANALOGS OF SOMATOSTATIN

[75] Inventors: Jean E. F. Rivier; Wylie W. Vale, Jr., both of La Jolla; Marvin R. Brown, Del Mar, all of Calif.

[73] Assignee: The Salk Institute for Biological Studies, San Diego, Calif.

[21] Appl. No.: 378,748

[22] Filed: May 17, 1982

[51] Int. Cl.³ .................... A61K 37/00; C07C 103/52
[52] U.S. Cl. ................... 424/177; 260/112.5 S
[58] Field of Search ................. 260/112.5 S; 424/177

[56] References Cited

U.S. PATENT DOCUMENTS

| Re. 30,548 | 3/1981 | Vale, Jr. et al. | 260/8 |
|---|---|---|---|
| 3,842,067 | 10/1974 | Sarantakis | 260/112.5 S |
| 3,933,784 | 1/1976 | Sarantakis | 260/112.5 S |
| 3,991,041 | 11/1976 | Garsky | 260/112.5 S |
| 4,011,207 | 3/1977 | Sarantakis | 260/112.5 S |
| 4,055,553 | 10/1977 | Chai et al. | 260/112.5 S |
| 4,061,607 | 12/1977 | Shields | 260/8 |
| 4,061,626 | 12/1977 | Shields | 260/112.5 S |
| 4,100,117 | 7/1978 | Shields | 260/112.5 S |
| 4,105,603 | 8/1978 | Vale, Jr. et al. | 260/112.5 S |
| 4,118,380 | 10/1978 | Immer et al. | 260/112.5 S |
| 4,133,782 | 1/1979 | Vale, Sr. et al. | 260/112.5 S |
| 4,159,263 | 6/1979 | Garsky | 260/112.5 S |
| 4,185,010 | 1/1980 | Sarantakis | 260/112.5 S |
| 4,190,575 | 2/1980 | Sarantakis | 260/112.5 S |
| 4,209,441 | 6/1980 | Lapidus et al. | 260/112.5 S |
| 4,210,636 | 7/1980 | Lien et al. | 260/112.5 S |
| 4,225,472 | 9/1980 | Sarantakis | 260/112.5 S |
| 4,282,143 | 8/1981 | Sarantakis | 260/112.5 S |
| 4,310,518 | 1/1982 | Freidinger et al. | 260/112.5 S |
| 4,328,214 | 5/1982 | Rink et al. | 260/112.5 S |
| 4,358,439 | 11/1982 | Siebey et al. | 260/112.5 S |

Primary Examiner—Delbert R. Phillips
Attorney, Agent, or Firm—Fitch, Even, Tabin & Flannery

[57] ABSTRACT

Somatostatin-14 has the formula:

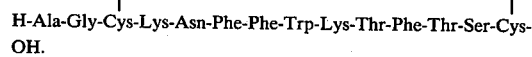

H-Ala-Gly-Cys-Lys-Asn-Phe-Phe-Trp-Lys-Thr-Phe-Thr-Ser-Cys-OH.

Analogs that are more potent than somatostatin-14 in increasing electrolyte absorption in the gut without suppressing the secretion of GH, insulin and glucagon, or pharmaceutically acceptable salts thereof, dispersed in a pharmaceutically acceptable liquid or solid carrier, can be administered to mammals in the same manner as somatostatin to increase absorbtion of electrolytes for the treatment of diarrhea. In particular of the analogs, certain substitutions are made for Phe in the 11-position, sometimes in combination with deletions in the 4- and 5-positions and in the 12- and 13-positions. D-Cys may also be substituted in the 3- or 14-position. There may be some substitutions in the 6- and 10-positions, and the residues in the 1- and/or 2-positions may also be deleted or substituted.

19 Claims, No Drawings

ANALOGS OF SOMATOSTATIN

This invention was made with Government support under Grant Nos. AM20917 and AM26741 awarded by DHHS(NIH). The Government has certain rights in this invention.

This invention is directed to peptides related to the tetradecapeptide somatostatin and to methods for pharmaceutical treatment of mammals using such peptides. More specifically, the invention relates to methods of treatment of mammals using somatostatin analogs which increase electrolyte absorption in the gut and also to certain analogs of somatostatin and to pharmaceutical compositions containing such analogs.

BACKGROUND OF THE INVENTION

The tetradecapeptide somatostatin was characterized by Guillemin et al. and is described in U.S. Pat. No. 3,904,594 (Sept. 9, 1975). The tetradecapeptide has the formula:

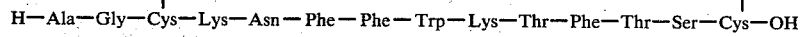
H—Ala—Gly—Cys—Lys—Asn—Phe—Phe—Trp—Lys—Thr—Phe—Thr—Ser—Cys—OH wherein there is a bridging bond between the sulfhydryl groups of the two cysteinyl amino acid residues. The tetradecapeptide in its linear form (sometimes referred to as dihydrosomatostatin), as well as analogs wherein this bridging bond is not present and is replaced by hydrogen, are for purposes of this application considered to be included in the definition "somatostatin analogs" as they appear to have substantially the same biological activity.

Somatostatin and many analogs of somatostatin exhibit activity in respect to the inhibition of growth hormone(GH) secretion from cultured, dispersed rat anterior pituitary cells in vitro and also in vivo, and with respect to the inhibition of insulin and glucagon secretion in vivo in the rat and in other mammals. Somatostatin has also been found to inhibit the secretion of gastrin and secretion by acting directly upon the secretory elements of the stomach and pancreas respectively. Its ability to inhibit the secretion of such hormones, allows somatostatin to be therapeutically employed in clinical conditions for the treatment of acromegaly, pancreatic islet cell tumors, diabetes mellitus and gastrointestinal bleeding. Because somatostatin has these properties, they must be taken into consideration whenever it is administered in vivo. The search has continued for somatostatin analogs which are potent in their effect in the gut but which are less potent than somatostatin in their inhibitory functions.

SUMMARY OF THE INVENTION

It has been found that diarrhea and the like can be effectively treated by the administration of analogs of the peptide somatostatin that have been prepared and purified (i.e., substantially free of related synthetic replicates) and which increase electrolyte absorption in the gut but which are very substantially less potent than somatostatin in inhibiting the release of GH, glucagon and/or insulin. This is referred to as having dissociated biological activity with respect to SS-14. The analogs have the formula:

R-$R_1$-$R_2$-Cys-$R_4$-$R_5$-$R_6$-Phe-Trp-Lys-$R_{10}$-$R_{11}$-$R_{12}$-$R_{13}$-Cys-OH wherein: R is hydrogen or an acylating agent selected from the group consisting of amino acids, dipeptides, tripeptides and aliphatic, aromatic and cyclic organic acids having from 1 to 10 carbon atoms; $R_1$ is Ala or des $R_1$; $R_2$ is Gly or des $R_2$; $R_4$ is Lys or D-Lys or des $R_4$; $R_5$ is Asn or des $R_5$; $R_6$ is Phe or D-Phe or Ala; $R_{10}$ is Thr or Ala or des $R_{10}$; $R_{11}$ is Ala, Arg, Trp, Val, Ile, Ser, Thr, Glu, His, $\beta$-Nal, Lys, Pro or des $R_{11}$; $R_{12}$ is Thr or Ala or des $R_{12}$; and $R_{13}$ is Ser or D-Ser or des $R_{13}$; provided that not more than two of $R_{10}$, $R_{11}$, $R_{12}$ and $R_{13}$ are deleted and provided that if $R_4$ is deleted, either $R_{12}$ or $R_{13}$ is deleted.

Pharmaceutical compositions in accordance with the invention include specific of these analogs, or nontoxic addition salts thereof, dispersed in a pharmaceutically acceptable liquid or solid carrier. The administration of such somatostatin analogs or pharmaceutically acceptable addition salts thereof to mammals in accordance with the invention may be carried out to increase the absorption of electrolytes and thereby effectively treat diarrhea in patients with endocrine tumors and short bowel syndrome.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. Where the amino acid residue has isomeric forms, it is the L-form of the amino acid that is represented unless otherwise expressly indicated. By $\beta$-Nal is meant 3-(naphthyl)-Ala.

The invention provides analogs of having the following formula:

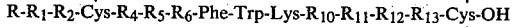
R-$R_1$-$R_2$-Cys-$R_4$-$R_5$-$R_6$-Phe-Trp-Lys-$R_{10}$-$R_{11}$-$R_{12}$-$R_{13}$-Cys-OH wherein: R is hydrogen or an acylating agent selected from the group consisting of amino acids, dipeptides, tripeptides and aliphatic, aromatic and cyclic organic acids having from 1 to 10 carbon atoms; $R_1$ is Ala or des $R_1$; $R_2$ is Gly or des $R_2$; $R_4$ is Lys or D-Lys or des $R_4$; $R_5$ is Asn or des $R_5$; $R_6$ is Phe or D-Phe or Ala; $R_{10}$ is Thr or Ala or des $R_{10}$; $R_{11}$ is Ala, Arg, Trp, Val, Ile, Ser, Thr, Glu, His, $\beta$-Nal, Lys, Pro or des $R_{11}$; $R_{12}$ is Thr or Ala or des $R_{12}$; and $R_{13}$ is Ser or D-Ser or des $R_{13}$; provided that not more than two of $R_{10}$, $R_{11}$, $R_{12}$ and $R_{13}$ are deleted and provided that if $R_4$ is deleted, either $R_{12}$ or $R_{13}$ is also deleted. Although not specifically shown herein, the formula should be understood also to include the linear form thereof wherein the bridge between the sulfhydryl groups of Cys residues is not present and is replaced by hydrogen. Of particular interest are the analogs where $R_{11}$ is Trp, Arg, His, β-Nal or Glu, with the first four being preferred.

The peptides are synthesized by a suitable method, such as by exclusively solid-phase techniques, by partial solid-phase techniques, by fragment condensation or by classical solution addition. For example, the techniques of exclusively solid-state synthesis are set forth in the textbook "Solid-Phase Peptide Synthesis", Stewart & Young, Freeman & Co., San Francisco, 1969 and are exemplified by the disclosure of U.S. Pat. No. 4,105,603, issued Aug. 8, 1978 to Vale et al. The fragment condensation method of synthesis is exemplified in U.S. Pat. No. 3,972,859 (Aug. 3, 1976). Other available syntheses are exemplified by U.S. Pat. No. 3,842,067 (Oct. 15, 1974) and U.S. Pat. No. 3,862,925 (Jan. 28, 1975).

Common to such syntheses is the protection of the labile side chain groups of the various amino acid moieties with suitable protecting groups which will prevent a chemical reaction from occurring at that site until the group is ultimately removed. Usually also common is the protection of an alpha-amino group on an amino acid or a peptide fragment while that entity reacts at the carboxyl group, followed by the selective removal of the alpha-amino protecting group to allow a subsequent reaction to take place at that location. Accordingly, it is common that, as a step in the synthesis, an intermediate compound is produced which includes each of the amino acid residues located in its desired sequence in the peptide chain with various of these residues linked to the side-action protecting groups.

Also considered to be within the scope of the present invention are intermediates of the formula:

$X^1$-$R_1$-$R_2$-Cys($X^2$)-$R_4$($X^3$)-$R_5$($X^4$)-Phe-Phe-Trp-Lys($X^3$)-$R_{10}$($X^5$)-$R_{11}$($X^6$)-$R_{12}$($X^5$)-$R_{13}$($X^5$)-Cys($X^2$)-$X^7$ wherein: the R-groups are as hereinbefore defined except for $R_{11}$ which is Trp, Arg, His, Glu or β-Nal and wherein:

$X^1$ is either hydrogen or an α-amino protecting group. The α-amino protecting groups contemplated by $X^1$ are those known to be useful in the art in the stepwise synthesis of polypeptides. Among the classes of α-amino protecting groups covered by $X^1$ are (1) acyl-type protecting groups, such as formyl, trifluoroacetyl, phthalyl, p-toluenesulfonyl(Tos), benzenesulfonyl, nitrophenylsulfenyl, tritylsulfenyl, o-nitrophenoxyacetyl, chloroacetyl, acetyl, and γ-chlorobutyryl; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as cyclopentyloxycarbonyl, adamantyloxycarbonyl, and cyclohexyloxycarbonyl; (5) thiourethan-type protecting groups, such as phenylthiocarbonyl; (6) alkyl-type protecting groups, such as triphenylmethyl(trityl), benzyl(Bzl); (7) trialkylsilane groups, such as trimethylsilane. The preferred α-amino protecting group is BOC.

$X^2$ is a protecting group for Cys preferably selected from the class consisting of p-methoxybenzyl(MeOBzl), p-methylbenzyl, acetamidomethyl, trityl and Bzl. The most preferred protecting group is p-methoxybenzyl. $X^2$ can also be hydrogen, meaning that there is no protecting group on the sulfur.

$X^3$ is hydrogen or a protecting group for the side chain amino substituent of Lys. Illustrative of suitable side chain amino protecting groups are Z, 2-chlorobenzyloxycarbonyl(2-Cl-Z), Tos, t-amyloxycarbonyl and BOC. The selection of a side chain amino protecting group is not critical except that it must be one which is not removed during deprotection of the α-amino groups during the synthesis. Hence, the α-amino protecting group and the side chain amino protecting group cannot be the same.

$X^4$ is hydrogen or a protecting group for the amido group of Asn and is preferably xanthyl(Xan).

$X^5$ is a protecting group for the hydroxyl group of Thr or Ser and is preferably selected from the class consisting of acetyl(Ac), benzoyl(Bz), tert-butyl, trityl, tetrahydropyranyl, benzyl ether(Bzl), 2,6-dichlorobenzyl and Z. The most preferred protecting group is Bzl. $X^5$ can be hydrogen, which means there is no protecting group on the hydroxyl group.

$X^6$ may be a protecting group for the guanidino group of Arg, if Arg is employed, preferably selected from the class consisting of nitro, Tos, Z, adamantyloxycarbonyl and BOC, or is hydrogen. Tos is most preferred. Otherwise, $X^6$ is a side chain protecting group for Glu or His, such as 2,6 dichlorobenzyl or Tos, respectively, if either of these residues is employed.

$X^7$ is selected from the class consisting of OH, OCH$_3$, amides, hydrazides and esters, including a benzyl ester or a hydroxymethyl ester anchoring bond used in solid phase synthesis for linking to a solid resin support, represented by the formulae:

—O—CH$_2$—polystyrene resin support and

O—CH$_2$—benzyl-polystyrene resin support

The polystyrene polymer is preferably a copolymer of styrene with about 0.5 to 2% divinyl benzene as a crosslinking agent, which causes the polystyrene polymer to be completely insoluble in certain organic solvents.

In the formula for the intermediate, at least one of $X^1$, $X^2$, $X^3$, $X^4$, $X^5$, $X^6$ and $X^7$ is a protecting group. In selecting a particular side chain protecting group to be used in the synthesis of the peptides, the following rules are followed: (a) the protecting group must be stable to the reagent and under the reaction conditions selected for removing the α-amino protecting group at each step of the synthesis, (b) the protecting group must retain its protecting properties and not be split off under coupling conditions and (c) the side chain protecting group must be removable, upon the completion of the synthesis containing the desired amino acid sequence, under reaction conditions that will not alter the peptide chain.

The peptides are preferably prepared using solid phase synthesis, such as that described by Merrifield, J. Am. Chem. Soc., 85, p 2149 (1964), although other equivalent chemical syntheses known in the art can also be used as previously mentioned. Solid-phase synthesis is commenced from the C-terminal end of the peptide by coupling a protected α-amino acid to a suitable resin. Such a starting material can be prepared by attaching α-amino- and S-protected Cys to a chloromethylated resin or to a hydroxymethyl resin. The preparation of the hydroxymethyl resin is described by Bodansky et al., *Chem. Ind.* (London) 38, 1597-98 (1966). Chloromethylated resins are commercially available from Bio Rad Laboratories, Richmond, Calif. and from Lab. Systems, Inc. The preparation of such a resin is described by Stewart et al., "Solid Phase Peptide Synthesis" (Freeman & Co., San Francisco 1969), Chapter 1, pp 1-6.

Cys protected by BOC and by p-methoxybenzyl is coupled to the chloromethylated polystyrene resin according to the procedure of Monahan and Gilon, *Biopolymer* 12, pp 2513-19, 1973. Following the coupling of BOC-(p-methoxybenzyl) (Cys) to the resin support, the α-amino protecting group is removed, as by using trifluoroacetic acid(TFA) in methylene chloride, TFA alone or with HCl in dioxane. Preferably 50 weight % TFA in methylene chloride is used with 0-5 weight % 1,2 ethane dithiol. The deprotection is carried out at a temperature between about 0° C. and room temperature. Other standard cleaving reagents and conditions for removal of specific α-amino protecting groups may be used as described in Schroder & Lubke, "The Peptides", 1 pp 72-75 (Academic Press 1965).

After removal of the α-amino protecting group of Cys, the remaining α-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as a coupling reagent is N,N'-dicyclohexyl carbodiimide (DCCI).

The activating reagents used in the solid phase synthesis of the peptides are well known in the peptide art. Examples of suitable activating reagents are:

(1) carbodiimides, such as N,N'-diisopropyl carbodiimide, N-ethyl-N'-(3-dimethylaminopropyl)carbodiimide; (2)cyanamides such as N,N'-dibenzylcyanamide; (3) keteimines; (4) isoxazolium salts, such as N-ethyl-5-phenyl isoxazolium-3'-sulfonate; (5) monocyclic nitrogen-containing heterocyclic amides of aromatic character containing one through four nitrogens in the ring, such as imidazolides, pyrazolides, and 1,2,4-triazolides. Specific heterocyclic amides that are useful include N,N'-carbonyl diimidazole, N,N'-carbonyl-di-1,2,4-triazole; (6) alkoxylated acetylene, such as ethoxyacetylene; (7) reagents which form a mixed anhydride with the carboxyl moiety of the amino acid, such as ethylchloroformate and isobutylchloroformate and (8) nitrogen-containing heterocyclic compounds having a hydroxy group on one ring nitrogen, such as N-hydroxyphthalimide, N-hydroxysuccinimide and 1-hydroxybenzotriazole(HOBT). Other activating reagents and their use in peptide coupling are described by Schroder & Lubke, supra, in Chapter III and by Kapoor, *J. Phar. Sci.*, 59, pp 1-27 (1970).

Each protected amino acid or amino acid sequence is introduced into the solid phase reactor in about a two- to fourfold excess, and the coupling is carried out in a medium of dimethylformamide(DMF):CH2Cl2 (1:1) or in DMF or CH2Cl2 alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the α-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927-1938.

After the desired amino acid sequence has been completed, the intermediate peptide is removed from the resin support by treatment with a reagent, such as liquid hydrogen fluoride or an equivalent, which not only cleaves the peptide from the resin but also cleaves all remaining side chain protecting groups $X^2$, $X^3$, $X^4$, $X^5$ and $X^6$ and the α-amino protecting group $X^1$, to obtain the peptide in its linear form. The cyclic form of the peptide is obtained by oxidizing using a ferricyanide solution, preferably as described Rivier et al., *Biopolymers*, Vol. 17 (1978), 1927-38, or by air oxidation, or in accordance with other known procedures.

As an alternative route, the intermediate peptide may be separated from the resin support by alcoholysis after which the recovered C-terminal ester is converted to the acid by hydrolysis. Any side chain protecting groups may then be cleaved as previously described or by other known procedures, such as catalytic reduction (e.g., Pd on BaSO4) using conditions which will keep the Trp moiety intact. When using hydrogen fluoride for cleaving, anisole and methylethyl sulfide are included in the reaction vessel for scavenging.

The following Example sets forth the preferred method for synthesizing analogs of somatostatin by the solid-phase technique.

EXAMPLE I

The synthesis of the analog [Trp$^{11}$]-SS having the formula:

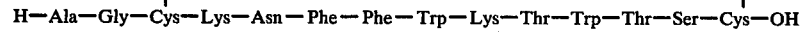

H—Ala—Gly—Cys—Lys—Asn—Phe—Phe—Trp—Lys—Thr—Trp—Thr—Ser—Cys—OH is conducted in a stepwise manner on a chloromethylated resin, such as LS-601 available from Lab Systems, Inc., containing 0.9 Meq Cl/gm. resin. Coupling of BOC-(p-methoxybenzyl)Cys to the resin is performed by the procedure set forth by Horiki et al., in *Chemistry Letters* (Chem. Soc. of Japan) (1978) pp. 165-168, and it results in the substitution of about 0.35 mmol. Cys per gram of resin. All solvents that are used are carefully degassed, preferably by sparging with an inert gas, e.g., nitrogen, to insure the absence of oxygen that might undesirably oxidize the Trp residue.

After deprotection and neutralization, the peptide chain is built step-by-step on the resin. Generally, one to two mmol. of BOC-protected amino acid in methylene chloride is used per gram of resin, plus one equivalent of 2 molar DCCI in methylene chloride, for two hours. When BOC-Trp or BOC-Arg(Tos) or BOC-Asn(Xan) is being coupled, a mixture of 10% DMF and methylene chloride is used. Bzl is used as the hydroxyl side-chain protecting group for Ser and Thr. P-nitrophenyl ester-(ONp) is used to activate the carboxyl end of Asn, and BOC-Asn(ONp) is coupled overnight using one equivalent of HOBt in a 50% mixture of DMF and methylene chloride. 2-Cl-Z is used as the protecting group for the Lys side chain. The amido group of Asn is protected by Xan. At the end of the synthesis, the following composition is obtained (BOC)Ala-Gly-Cys(MeOBzl)-Lys(2-Cl-Z)-Asn(Xan)-Phe-Phe-Trp-Lys(2-Cl-Z)-Thr(Bzl)-Trp-Thr(Bzl)-Ser(Bzl)-Cys(MeOBzl)-O-CH$_2$-benzyl-polystyrene resin support.

In order to cleave deprotect the resulting protected peptide-resin, it is treated with 1.5 ml. anisole, and 15 ml. hydrogen fluoride(HF) per gram of peptide-resin, first at $-20°$ C. for 20 min. and then at 0.° C. for one-half hour. After elimination of the HF under high vacuum, the resin-peptide is washed alternately with dry diethyl ether and chloroform, and the peptides are then extracted with de-gassed 2 N aqueous acetic acid and separated from the resin by filtration.

The cleaved and deprotected peptide is then and added dropwise to a potassium ferricyanide solution to form the disulfide bond between the Cys residues, as described by Rivier et al. in *Biopolymers*, Volume 17 (1978) pp. 1927–1938. After cyclization, the peptide is chromatographed on both anion- and cation-exchange resins using the methods described in the Rivier et al. article and then lyophilized.

The peptide is then purified by gel permeation followed by semi-preparative HPLC as described in Rivier et al., *Peptides: Structure and Biological Function* (1979) pp. 125–128. The chromatographic fractions are carefully monitored by HPLC, and only the fractions showing substantial purity were pooled.

Specific optical rotation of the SS analog, which was synthesized and purified in the foregoing manner, was measured on a Perkin Elmer Model 141 as $[\alpha]_D^{22°} = -34.5°$ (c=1 in 1% acetic acid) and had a purity of about 95%. To check whether the precise sequence was achieved, the analog was hydrolyzed in sealed evacuated tubes containing 4 N methanesulfonic acid and 0.2% tryptamine for 24 hours at 110° C. Amino acid analyses of the hydrolysates using a Beckman 121 MB amino acid analyzer showed that the 14-residue peptide structure had been obtained.

The other analogs listed in Table I are also synthesized and purified using the same method as set forth above.

TABLE I

| No. | Composition |
|-----|-------------|
| 1 | [Trp$^{11}$]—SS |
| 2 | [Arg$^{11}$]—SS |
| 3 | des-AA$^{1,2}$,[Trp$^{11}$]—SS |
| 4 | des-AA$^{1,2,4,5,12}$,[D-Trp$^8$,Trp$^{11}$]—SS |
| 5 | [Ala$^{11}$]—SS |
| 6 | des-AA$^{1,2,4,5,12}$,[D-Trp$^8$]—SS |
| 7 | des-Thr$^{12}$—SS |
| 8 | des-Phe$^{11}$—SS |
| 9 | des-Ala$^1$,Gly$^2$—SS |
| 10 | [His$^{11}$]—SS |
| 11 | des-AA$^{1,2}$,[$\beta$-Nal$^{11}$]—SS |
| 12 | [Glu$^{11}$]—SS |
| 13 | des-Asn$^5$—SS |
| 14 | des-Ser$^{13}$—SS |
| 15 | [D-Lys$^4$]—SS |
| 16 | [D-Phe$^6$]—SS |
| 17 | [D-Cys$^{14}$]—SS |

EXAMPLE II

To determine the effectiveness of the peptides to inhibit the release of growth hormone, in vitro radioimmunoassays are carried out using the SS analogs in side-by-side comparison with equimolar concentrations of somatostatin-14 having a known effectiveness to inhibit the release of growth hormone induced by the application of isobutyl methyl xanthine to pituitary cells. Cultures are used which include cells of rat pituitary glands removed some four to five days previously in a system that minimizes enzymatic degradation, generally following the procedure set forth in Vale et al., *Methods in Enzymology, Hormones and Cyclic Nucleotides* (1975) Vol. 37, p. 82. Both cultures of a defined standard medium and cultures which are considered optimal for the secretion of growth hormone, as a result of having additions of either 2% or 10% of serum from a foetal calf, are used for the comparative testing. The result of this comparative testing is that analog No. 1 shows a potency for the inhibition of GH less than about 1% of that of SS-14.

In vivo experiments are carried out with the analogs, using the procedure described in Brown et al., *Metabolism* (1976) Vol. 25, pp. 1501–1503, to determine the potency, relative to somatostatin-14, to inhibit the secretion of glucagon and insulin stimulated by the administration of arginine to groups of six rats. Analog No. 1 exhibits a potency to inhibit basal and stimulated insulin and glucagon secretion in mammals, including humans and dogs, less than about 1% and 1% respectively, compared to SS-14. The remaining peptide analogs have similar significantly reduced effects upon the inhibition of GH, insulin and glucagon release.

The analogs are tested in vitro in isolated rabbit ileum using the modified Ussing chamber technique, as described in *Amer. J. of Physiol.*, 225:776–780 (1973). Unidirectional chloride fluxes are determined and used to characterize bi-directional fluxes following the addition of an SS-analog. Changes are measured with varying concentrations, and the potency to inhibit ion transport is quantitated and expressed as a percentage of the potency of SS-14. For example, analog No. 1 shows a potency about 249% of that of SS-14 which is indicative of its effectiveness in increasing electrolyte absorption in the gut. All of the analogs either show a very substantial increase in electrolyte absorption in the gut without increasing the inhibition of other secretions, or show a far greater decrease in the inhibition of the secretion of insulin, glucagon and/or GH than in its biological activity in the gut. These results are summarized in Table II.

| Peptide | Insulin | Glucagon | GH | Ion Transport |
|---------|---------|----------|-----|---------------|
| SS-14 | 100 | 100 | 100 | 100 |
| 1 | <1 | <1 | <1 | 249 |
| 2 | 142 | <1 | | 291 |
| 3 | | | | 405 |
| 4 | | | | 37 |
| 5 | <10 | | 3 | 52 |
| 6 | 70 | 20 | 45 | 257 |
| 7 | <1 | <1 | 2 | 21 |
| 8 | <1 | <1 | 2 | 34 |
| 9 | 61 | | 60 | 231 |
| 10 | <1 | <1 | | 48 |
| 11 | | | | 107 |
| 12 | <1 | <1 | | 9 |
| 13 | 10 | <1 | 4 | 11 |
| 14 | <1 | <1 | 2 | 9 |
| 15 | 1 | 1 | 22 | 139 |
| 16 | <1 | <1 | 5 | 10 |
| 17 | 20 | 310 | 270 | 336 |

The administration to mammals of an effective amount of these analogs (or a nontoxic, pharmaceutically aceptable addition salt thereof) can be used to very substantially increase electrolyte absorption and decrease gut motility in mammals and may be employed in the treatment of diarrhea, in the same general manner as somatostatin is presently being administered for inhibiting gastric secretion, particularly in patients with carcinoid tumors and short bowel syndrome. Likewise, administration of these peptides to mammals in effective amounts can be used to increase the absorption of electrolytes in the gut without significantly inhibiting the release of growth hormone, insulin or glucagon and can be used for this purpose, under the guidance of a physician, generally along the lines and in accordance with clinical procedures heretofore developed using somatostatin-14 for the purpose of decreasing gastric acid secretion.

It was very surprising to discover that certain of these analogs exhibited such a substantial increase in electrolyte absorption, in comparision with SS-14, while having very significantly less effect upon the inhibition of GH, insulin and glucagon secretion. As a result, these peptide analogs are particularly valuable for the treatment of diarrhea which can be carried out without undesirable side effects that would accompany treatment with larger dosages of SS-14 for this purpose.

These analogs or the nontoxic addition salts thereof, combined with a pharmaceutically acceptable carrier to form a pharmaceutical composition, may be administered to mammals, including humans, either intravenously, subcutaneously, intramuscularly, intranasally or orally. The administration may be employed by a physician to treat diarrheal syndrones. The required dosage will vary with the particular condition being treated, with the severity of the condition, with the duration of desired treatment and with the method of administration. Intravenous administration is preferred because it has about the same effect as a dose given orally one thousand times greater or a dose given intranasally one hundred times greater.

The peptides should be administered under the guidance of a physician, and pharmaceutical compositions will usually contain the peptide in conjunction with a conventional, sterile liquid pharmaceutically-acceptable carrier. Usually, the intravenous administration for a patient of normal body weight will be from 25 to 300 μg/hr. for as long as necessary to alleviate the diarrheal syndrone, e.g., for a 24-hour period. Overall, treatment of subjects with these peptides is generally carried out in the same manner as the treatment for gastric ulcers is presently carried out using somatostatin itself.

Such peptides are often administered in the form of pharmaceutically acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, pamoate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at positions in the somatostatin peptide chain which are indicated as being presently subject to deletion, as well as in the 6-position, can be made with other naturally occuring amino acids without detracting from the potency of the analogs, and such peptides are considered as being within the scope of the invention. As earlier indicated, the linear form as well as the preferred cyclic form of the analogs is considered to be within the scope of the invention, and the two-member tail (i.e., Ala-Gly) can be deleted, substituted, modified or substantially added to without adversely affecting the potency of the analogs, as set forth in Guillemin et al. U.S. Pat. No. 3,904,594 which describes the addition of an acylating agent.

Various features of the invention are emphasized in the claims which follow.

What is claimed is:

1. A method for the treatment of mammals to increase electrolyte absorption in the gut comprising administering an effective amount of a somatostatin analog having the formula:

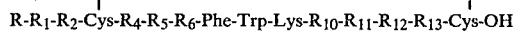

$$R-R_1-R_2-Cys-R_4-R_5-R_6-Phe-Trp-Lys-R_{10}-R_{11}-R_{12}-R_{13}-Cys-OH$$

wherein: R is hydrogen; $R_1$ is Ala or des $R_1$; $R_2$ is Gly or des $R_2$; $R_4$ is Lys or D-Lys or des $R_4$; $R_5$ is Asn or des $R_5$; $R_6$ is Phe or D-Phe or Ala; $R_{10}$ is Thr or Ala or des $R_{10}$; $R_{11}$ is Ala, Arg, Trp, Val, Ile, Ser, Thr, Glu, His, β-Nal, Lys Pro or des $R_{11}$; $R_{12}$ is Thr or Ala or des $R_{12}$; and $R_{13}$ is Ser or D-Ser or des $R_{13}$; provided that not more than two of $R_{10}$, $R_{11}$, $R_{12}$ and $R_{13}$ are deleted and provided that if $R_4$ is deleted, either $R_{12}$ or $R_{13}$ is also deleted; or a nontoxic addition salt thereof.

2. The method of claim 1 wherein $R_{11}$ is Trp.

3. The method of claim 1 wherein $R_{11}$ is Arg.

4. The method of claim 1 wherein $R_{11}$ is β-Nal.

5. The method of claim 1 wherein $R_{11}$ is His.

6. The method of claim 2 wherein Trp in the 8-position is D-Trp.

7. The method in accordance with claim 1 wherein said administering is carried out either orally, intravenously, subcutaneously, intranasally or intramuscularly.

8. The method in accordance with claim 1 where said administering is carried out intravenously at between 25 and 300 μg per hour.

9. A pharmaceutical composition for administration to mammals for the treatment of diarrhea, which comprises an effective amount of a somatostatin analog having the formula:

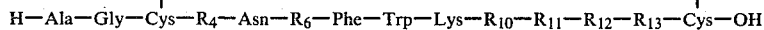

$$H-Ala-Gly-Cys-R_4-Asn-R_6-Phe-Trp-Lys-R_{10}-R_{11}-R_{12}-R_{13}-Cys-OH$$